United States Patent
Burtscher et al.

(10) Patent No.: US 7,549,318 B2
(45) Date of Patent: Jun. 23, 2009

(54) METHOD AND DEVICE FOR THE MEASUREMENT OF THE NUMBER CONCENTRATION AND OF THE AVERAGE DIAMETER OF AEROSOL PARTICLES

(75) Inventors: Heinz Burtscher, Rudolfstetten (CH); Martin Fierz, Zürich (CH)

(73) Assignee: Matter Engineering, Wohlen (CH)

( * ) Notice: Subject to any disclaimer, the term of this patent is extended or adjusted under 35 U.S.C. 154(b) by 350 days.

(21) Appl. No.: 11/330,805

(22) Filed: Jan. 12, 2006

(65) Prior Publication Data
US 2006/0150754 A1 Jul. 13, 2006

(30) Foreign Application Priority Data
Jan. 13, 2005 (EP) ................... 05405015

(51) Int. Cl.
*G01N 15/06* (2006.01)
*G01N 15/02* (2006.01)
(52) U.S. Cl. ..................... 73/28.02; 73/865.5
(58) Field of Classification Search ............... 73/28.02, 73/865.5
See application file for complete search history.

(56) References Cited
U.S. PATENT DOCUMENTS

| | | | |
|---|---|---|---|
| 3,178,930 A * | 4/1965 | Moore et al. ............... | 73/28.02 |
| 3,526,828 A | 9/1970 | Whitby | |
| 3,763,428 A | 10/1973 | Preist | |
| 4,435,681 A | 3/1984 | Masuda et al. | |
| 4,574,004 A | 3/1986 | Schmidt-Ott et al. | |
| 4,959,010 A * | 9/1990 | Burtscher et al. ............. | 431/12 |
| 5,214,386 A | 5/1993 | Singer et al. | |
| 7,387,038 B2 * | 6/2008 | Wei et al. ................... | 73/865.5 |
| 2004/0083790 A1 * | 5/2004 | Carlson et al. ............. | 73/28.02 |

FOREIGN PATENT DOCUMENTS

| | | | | |
|---|---|---|---|---|
| DE | 198 24 744 A1 | 3/1999 | | |
| EP | 310348 A2 * | 4/1989 | ............... | 73/28.02 |
| EP | 1 156 320 A | 11/2001 | | |

OTHER PUBLICATIONS

Bukowiecki et al, "Real-time characterization of ultrafine and accumulation mode particles in ambient combustion aerosols", Journal of Aerosol Science, Aug. 2002, pp. 1139-1154, XP-002324115.

* cited by examiner

*Primary Examiner*—Thomas P Noland
(74) *Attorney, Agent, or Firm*—Rankin, Hill & Clark LLP

(57) ABSTRACT

According to the invention, particles of an aerosol are firstly charged in a unipolar manner in a diffusion charger (10). They are subsequently led through a diffusional precipitator (20) in which a part of the particles is precipitated. The diffusional precipitator current is measured and a value for the number concentration is evaluated from the current. A single diffusional precipitator may be used for this. According to preferred embodiment, a means for measuring the influence current and/or an aerosol electrometer are additionally present, by way of which one may measure a complete current. The latter additionally permits the evaluation of the average particle size. Additionally, one may determine an elementary carbon total quantity from the average particle size with the help of a measurement of the photoelectric charging carried out in parallel.

12 Claims, 4 Drawing Sheets

METHOD AND DEVICE FOR THE MEASUREMENT OF THE NUMBER CONCENTRATION AND OF THE AVERAGE DIAMETER OF AEROSOL PARTICLES

BACKGROUND OF THE INVENTION

The invention relates to a method and to a device for the measurement of the number concentration and/or of the average diameter of particles suspended in a carrier gas. It also relates to a method for measuring the elementary carbon quantity in an aerosol.

Particles suspended in carrier gases (aerosols) play a significant role in the atmosphere, breathing air and in many technical processes, for example in the emissions of combustion motors. The particles are often indicated both as suspended particles and as suspended dust. An important task lies in detecting the concentration of the particles by way of measurement technology. Particles in the size range of smaller than 10 micrometers diameter may be breathed in by humans and may have a detrimental effect on health. The most recent research results indicate that the usual protective functions of humans are no longer effective for nanoparticles<100 nm. Nanoparticles arise mainly in combustion processes such as in motor vehicles, coal-fired power stations, wood heating installations, etc.

Previous standards and guidelines mostly indicate the particle concentration in the form of particle mass per volume unit of the aerosol, for example in micrograms per cubic metre or, with emissions from motor vehicles, in mass per driven distance or per output of energy (μg/km, μg/kWh). The particle loading specified in such a manner practically only concerns particles which are larger than approx. 0.1 micrometers, since the smaller ones, which although occurring in a larger number concentration, do not carry any weight with regard to mass. Measurement methods which may detect the small particles with a suitable weighting are therefore of current importance. With these, it is the measurement of the particle number concentration which is significant. This for example is also demanded in the suggestions of a European commission of experts, for a limit value of emissions of diesel engines. The size range of interest in the case of diesel particles extends from a few nanometers to a few hundred nanometers. Still larger particles have no significant influence on the number concentration.

Nowadays, condensation nucleus counters (meters) are almost exclusively applied for measuring the particle number concentration (see for example Aerosol Measurement, Principles, Techniques and Applications, P. A. Baron and K. Willeke, Wiley, New York, 2001). With this, the particles are brought into an environment with an over-saturated vapour (e.g. butanol vapour). The vapour condenses on the particles, by which means these grow to such an extent, that they may be subsequently detected by light scattering measurements. The number of light flashes of the individual particles permits the concentration to be determined in a direct manner. This method is very sensitive and one may also measure extremely low concentrations. It however demands a strict adherence to the temperatures on production and condensation of the over-saturated vapour. On the one hand this renders it awkward and on the other hand dependent on the environmental conditions.

If information with regard to the size is also required, then systems based mainly on mobility analysis are applied, with which the drift speed of charged particles is measured in an electrical field. Most widespread is the scanning mobility particle sizer (SMPS, Wang, S. C. and R. C. Flagan: Scanning electrical mobility spectrometer. *Aerosol Sci. Technol.* 12, 1990, 230-240). It has a relatively good accuracy, but a size spectrum measurement lasts about 1-2 minutes. For 1-2 years now, there have been new types of apparatus which are based on a similar principle but which have a time resolution of ~0.1-1 s (EEPS of TSI, DMS of Cambustion). These apparatus however are large, heavy and expensive.

An apparatus for measuring size distributions based on diffusion was recently presented (EP 1 156320 A1). Here, the particles are first charged with a diffusion charger, and subsequently separated in several steps according to their size by diffusional precipitators, and electrically measured. One may determine size distributions of particles and thus also information on the particle number in each size class with this measurement principle. The apparatus however is comparatively complicated, and the evaluation of the measurements is cumbersome.

One parameter which is also important for evaluating the detriment to health is the elementary carbon value, i.e. the total quantity of elementary carbon present in particles. This is because the detrimental effect to health of the particles above all may be traced back to the carbon—mostly present in the form of polycyclic aromatics. It has already been suggested to use the principle of photoelectric charging for the measurement of the number of charged particles with polycyclic hydrocarbons on the surface. However, the total quality of elementary carbon may not be deduced from this without further ado.

BRIEF SUMMARY OF THE INVENTION

It is the object of the present invention to provide a method and a device for measuring the particle concentration or particle number and/or the average particle size, which overcomes the existing disadvantages of existing methods and which in particular permits rapid measurements with a comparatively less complex apparatus. A further object of the invention is to provide a method which permits the measurement of an elementary carbon value.

According to the invention, particles of an aerosol are first charged, for example, in a unipolar manner, in a diffusion charger. Subsequently they are led through a diffusional precipitator in which a part of the particles are precipitated. The diffusional precipitator current is measured and a value for the number concentration is determined from the current.

Hereinafter, the current produced in the diffusional precipitator by the charged aerosol particles is called "diffusional precipitator current".

It is a recognition of the invention, that the diffusional precipitator current, which is comparatively simple to measure, represents a measure of the particle number concentration. This is for the following reasons.

The average charge $\bar{q}$ which the particles obtain in the diffusion charger is proportional to the attachment (accumulation) cross section K of the particles:

$$\bar{q} \propto K$$

wherein K is a function of the particle size.

The probability of a particle being precipitated in the diffusional precipitator depends on the diffusion constant D of the particles. This in turn, in a good approximation, is inversely proportional to the attachment coefficient K (according to A. Keller, M. Fierz, K. Siegmann, and A. Filippov. *J. Vac Sci. Technol.* A 19.1 2001, 1-8).

$$D \propto K^{-1}$$

The diffusional precipitator current I which is caused by the precipitated particles in the diffusional precipitator is measured. It is determined from the product of precipitation probability, particle charging and particle concentration N, which is to say:

$$I \propto D \cdot \bar{q} \cdot N \propto K \cdot K^{-1} \cdot N \propto N$$

The two factors dependent on size compensate one another, the diffusional precipitator current then only continues to be dependent on the particle concentration, and thus according to the invention, may be used as a measure of the particle concentration.

The diffusion charger may, for example, be a unipolar diffusion charger. It may comprise an electrically shielded region with a high-voltage field in which ions are produced. These flow through openings in the electrical shielding (this is designed for example as a grid) into a region through which aerosol flows.

One uses a single diffusional precipitator in a particularly preferred embodiment of the invention. With such a precipitator, the surfaces at which the particles are precipitated and thereby contribute to a diffusion current are electrically connected to one another. Thus only a current measuring apparatus is necessary for detecting the diffusion current. As generally less preferred alternatives, also several surface regions electrically connected in parallel (i.e. the surface regions are for example each provided with an electrometer, and the readings evaluated by these are added, where appropriate, after calibration adaptation) or surface regions which are arranged in parallel with regard to flow (i.e. with different aerosol portions) are in each case connected to an electrometer. In contrast to the state of the art known from EP 1 156 320, where information may be determined by way of the number concentration, where appropriate indirectly via the size distribution, the method according to the invention makes do without a plurality of diffusional precipitators which are serially arranged. The procedure according to the invention therefore permits the use of a relatively simple apparatus for determining the number concentration.

The diffusional precipitator may be designed as a plate precipitator, a grid precipitator or a tube precipitator, as is known per se. Combinations of these principles are also conceivable, for example, the diffusional precipitator initially may have a plate design and subsequently a grid or tube arrangement electrically connected thereto, but other combinations are also conceivable.

If the particle concentration or size strongly vary with transient procedures, the flow of charged particles which reach the diffusional precipitators would fluctuate accordingly. Apart from the desired flow of precipitated particles, these fluctuations also effect an influence current which disturbs the measurement. In order to compensate this, one may also apply a means for measuring the influence additionally to the diffusional precipitators. Only the influence current is then measured. This then, when required, after a correction of the time delay with which the particles meet the two units, and multiplication by a correction factor which compensates different sensitivities, may be subtracted from the signal of the diffusional precipitator. The influence current may be compensated in this manner.

The means for measuring the influence may be arranged in a series arrangement before or after the diffusional precipitator. As an alternative, it may also be arranged in parallel, i.e. in each case a defined portion of the aerosol is led to the diffusional precipitator and to the influence measurement means.

Here and in the complete document, "parallel" is of course not to be understood geometrically, but relates to the nature of the relationship in which the individual means are arranged to one another with respect to the flow, or to how they are electrically connected.

The influence measurement means may look similar to the diffusional precipitator, but contains no precipitator plates, -tubes or -grids. It has for example the same geometric shape as the diffusional precipitator, wherein the dimensioning (for example the extension in the throughput direction or the absolute size) need not be identical. The electrode of the influence measurement means may be essentially applied at zero potential or may have the same electrical potential as the diffusional precipitator.

The influence current measurement of the previously described type may also be used in combination with measurements other that the evaluation of the particle number concentration by way of diffusional precipitation, inasmuch as currents produced by way of precipitation of charged aerosol particles on electrodes are measured in a transient process (thus in a process with non-stationary readings). Examples of these are measurements of particle size distribution as disclosed in EP 1 156 320, measurements by way of impactors or measurements by way of differential mobility analysers (DMA). Such measurements are based on an aerosol with charged particles flowing through a gas conducting arrangement and—where appropriate under the influence of physical and/or chemical effects (actions)—a portion of the charged particles is precipitated on precipitation surfaces connected to a first electrode. They are distinguished by the fact that a second electrode is present, which is preferably designed in a similar manner to the first electrode but which has no precipitation surfaces. The second electrode is arranged before or after the first electrode in the flow direction, or the electrodes are arranged in parallel as previously mentioned. Thereby, as with the previously mentioned embodiment of the invention, it is not necessary for the second electrode to be at a specific potential; it may for example be applied at zero potential or have the same potential as the first electrode.

According to a preferred embodiment of the invention, apart from an approximate value for the particle number concentration, one also determines information on the particle size. The average particle charge, specifically within a large size range, to a good approximation is proportional to $d^x$, wherein d is the particle diameter and the exponential x is roughly 1.2. This means that the total charge concentration $q_{tot}$ which the particles carry, is proportional to $Nd^x$. The total charge concentration may be determined when all particles are precipitated in a filter and the current $I_{tot}$ which they create there is measured.

If therefore a diffusional precipitator as well as a filter are used, one obtains a current I which is proportional to N, and a current $I_{tot}$ which is proportional to $Nd^x$. Thus the particle diameter d may be determined from the quotient of the two currents. Specifically the following applies:

$$d = c \cdot \left(\frac{I_{tot}}{I}\right)^{1/x}$$

The proportionality constant c may be determined by calibration or may be computed in an approximate manner when the geometry is known. If not only a particle size is present, but also a wide size distribution to a greater or lesser extent, one then obtains an average particle diameter by way of evaluating d. If the filter for measuring $I_{tot}$ is operated behind the diffusion charger (i.e. the aerosol or portions thereof flows or flow through the diffusional precipitator and the filter in a series arrangement consecutively), the diffusional precipitator current I measured in the diffusional precipitator has yet to be added to the current measured in the filter, in order to obtain the total current $I_{tot}$. Number concentration and average diameter may be determined with this arrangement. A parallel arrangement is also conceivable, where in each case a defined portion of the aerosol to be characterised is deflected through the diffusional precipitator or the filter.

As already mentioned, the above mentioned relationships are approximate. A certain dependency on size is present with a more accurate observation. The evaluation of the size from the currents I and $I_{tot}$ permits an at least partial compensation of this size dependency. Apart from the additional size information, accordingly the accuracy of the evaluation of the number concentration may also be improved if $I_{tot}$ is also measured. A size dependency determined in an experimental manner may also be taken into account.

According to a particular embodiment of the invention, the average diameter obtained in the measurement method is used in order to determine an elementary carbon total quantity. For this, a part of the aerosol to be characterised, in addition to the inventive measurement with diffusion charging, diffusional precipitation and total charging concentration measurement, is yet also charged photoelectrically and the photoelectric charging per unit of time is measured. This is effected in a parallel measurement line. Thus, a part flow from an aerosol flow to be characterised is led through a first measurement line with a diffusion charger and diffusional precipitator— and where appropriate further measurement apparatus, for example for measuring the influence, whilst another part flow is led through a second measurement line with a photoelectric charger and a device for measuring the total charging concentration—for example an aerosol electrometer.

As specified previously, one may determine the average diameter by way of the measurement in the first measurement line. This average diameter may be used in order to determine an elementary carbon value from the result of the photoemission measurement. This is because of the following considerations and relations.

As is known per se, the photoemission charging efficiency to the first degree is determined by the quantity of carbon present. The photoemission charging accordingly correlates well with the elementary carbon quantity.

It has been experimentally ascertained, that the charging factor depends on the particle size when a fixed quantity of carbon is represented in particle form and is suspended in a carrier gas. The dependency on the particle size is monotonic.

A method for determining the elementary carbon total quantity in an aerosol therefore comprises the steps of:

A determining an average particle diameter of the particles suspended in the aerosol B photoelectric charging of aerosol particles C determining a total charge (charging) of the photoelectrically charged aerosol particles D determining an elementary carbon total quantity from the average particle diameter and from the total charging.

Thereby, the following applies:

The method step A does not necessarily need to take place before the method steps B and C. Rather, according to a particularly preferred procedure, the method step A is carried out in a first, and the method steps B and C in a second measurement line, wherein from the aerosol flow to be characterised, a first part flow is led through the first measurement line and a second part flow through the second measurement line.

The method step A is preferably carried out with the previously described method for measuring the number concentration and/or the average diameter of particles. However this is not a necessary precondition. Indeed, the method step may be carried out with any other known or yet to be developed method for determining an average particle size.

A relation between the particle size, photoelectric charging and elementary carbon total quantity may for example be determined in that, in a first step, a known quantity of elementary carbon in particle form is represented and is suspended in a carrier gas, whereupon the previously mentioned method steps A-C are carried out on the aerosol which is formed by way of this. This is repeated for various particle sizes. Such measurements may be supplemented by other methods for particle characterisation. The function M=M(PE,d) resulting after a number of measurements (M=elementary carbon total quantity, for example in μg, PE=photoelectrical charging, d=average particle diameter), is dependent on the configuration of the photoelectric charger. It may, however, be approximated by $M=cM_{univ}$, wherein $M_{univ}$ is a generally valid function which is determined once, and c is a calibration factor dependent on the apparatus.

The device according to the invention comprises a gas conducting arrangement, in which an aerosol flows through the diffusion charger and then at least a part thereof flows through the diffusional precipitator. A possible influence current measurement means is arranged before or after the diffusional precipitator, and a possible filter for the measurement of the total charging is arranged after the diffusional precipitator as well as the influence current measurement means. As mentioned, alternatively to this series arrangement, one may also apply a parallel arrangement with which the aerosol is led in various lines, of which one comprises the diffusion charger and at least one another, for example, comprises the influence current measurement means and/or the filter for the total current measurement. The device may yet comprise conveying means, for example a pump, by way of which the throughput of aerosol is effected and controlled. Alternatively to this, the conveying may also be effected by external means, for example, with an exhaust gas measurement, by way of the flow advance produced by the motor.

BRIEF DESCRIPTION OF THE DRAWINGS

Embodiment examples of the invention are described in more detail by way of figures. In the figures, which are all schematic, there are shown in.

DETAILED DESCRIPTION OF THE INVENTION

Figure 1:
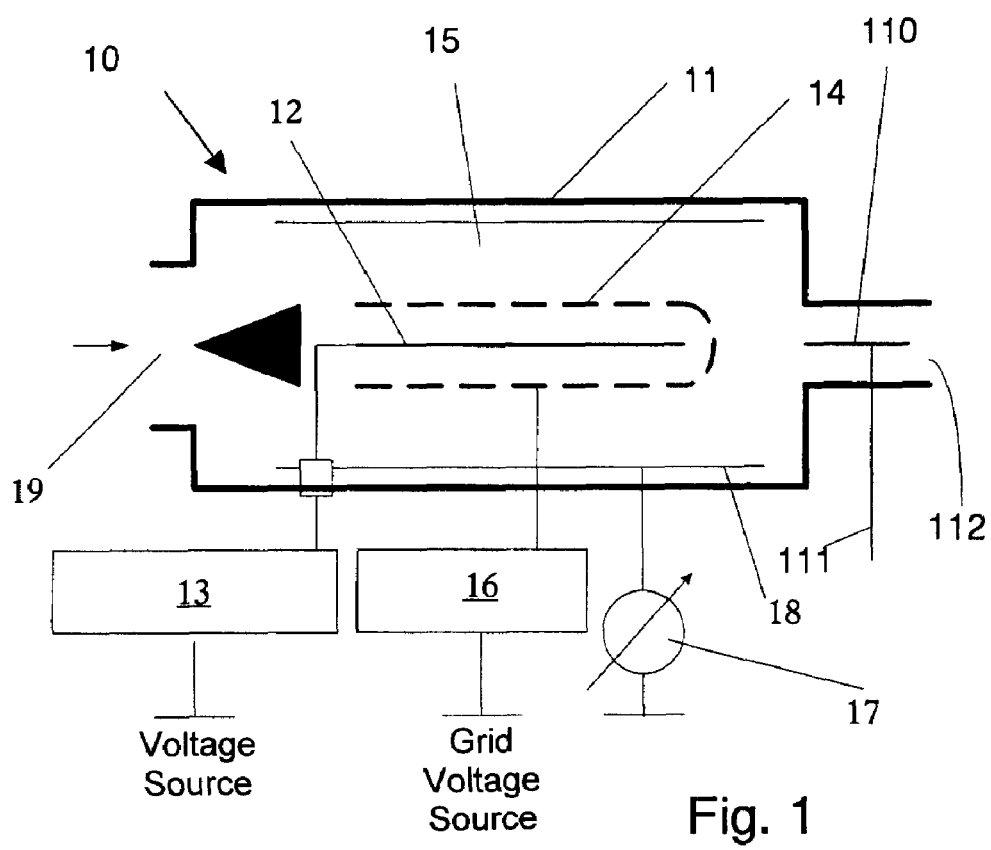
FIG. 1 a diffusion charger of a device according to the invention.

The charging may be effected by ions which are produced by electrical corona discharge. One possible configuration of a charger 1 is shown in FIG. 1. A thin wire 12 is arranged, in an axial manner, in a cylindrical housing 11 with an aerosol inlet 19 and an aerosol outlet 112. A high voltage 13 is applied to the wire, wherein the voltage is high enough so as to produce a corona electrical discharge from the wire. A grid arrangement 14 electrically shields the region in which the high voltage field prevails from the volume 15 through which the aerosol flows. The number of ions which get through the grid into the space 15 may be varied by way of a small voltage applied to this grid (by way of a voltage source 16), and may be measured by an ammeter 17 at an external electrode 18 at zero potential which surrounds the volume through which the aerosol flows. The efficiency of the charging may be determined by way of the selection of the voltage 16 prevailing at the grid. It should be as high as possible for the described application, but the voltage may not be selected too high, since otherwise charged particles are already deposited in the charger. It is typically between 5 V and 30 V. Ions which are not attached to particles and which could adulterate the measurement are precipitated by way of an ion trap at the exit of the charger. This ion trap may be a rod 110 which via a supply 111 is applied at a voltage which is high enough in order to precipitate the ions. Given a suitable choice of the electrical potential of the rod, charged particles are attached on the rod at a percentage which does not influence the measurements, due to the lower mobility.

Figure 2:
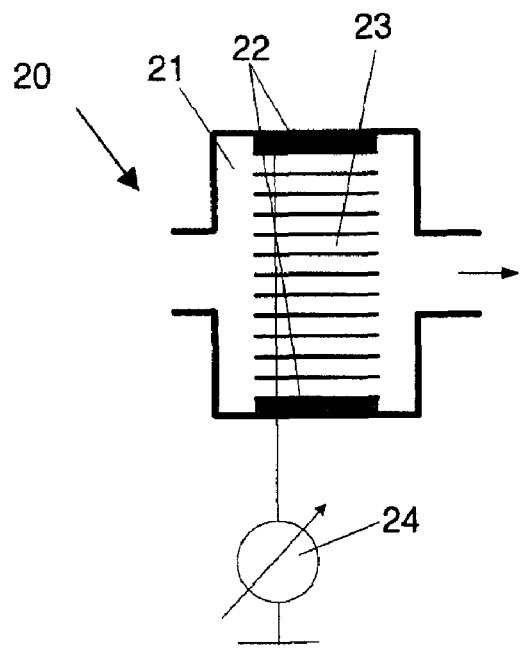
FIG. 2 a diffusional precipitator of a device according to the invention.

The diffusional precipitator 20 according to FIG. 2 may be designed as a plate bundle 23 which is mounted in a housing 21 in an insulated manner via an insulator 22 (plate precipitator). The current, which precipitated charged particles create on the plates, may be measured with an ammeter. Various other solution variants are possible instead of the plate bundle. The diffusional precipitator may, for example, also be designed as a tube bundle (tube precipitator) or as a honeycomb structure. Arrangements of one or more grids (grid precipitators) may also be applied. Many various embodiments of diffusional precipitators may be found from literature.

Figure 3:
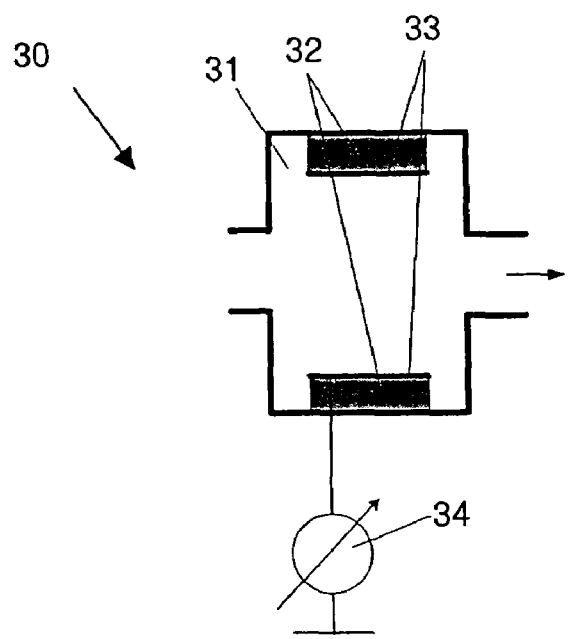
FIG. 3 a measurement arrangement for measuring the influence current.

An arrangement for measuring the influence current 30 is shown in FIG. 3. In a sealed, electrically conductive housing 31, the aerosol flows through an electrode 33 which is mounted in an insulated manner (insulator 32) and which is connected to an ammeter 34. The arrangement for measuring the influence current for example has the cylindrical (or also non-cylindrical) shape which is essentially identical to the diffusional precipitator, and for example also has the same dimensions, wherein of course the precipitation surfaces (plates, tubes, honeycomb, grids etc.) are absent. In such a configuration, the quantity of the particles precipitated at the electrode 33 is small in comparison to the influence current which is effected in this on account of changes of the total particle charging with transient procedures.

Figure 4:
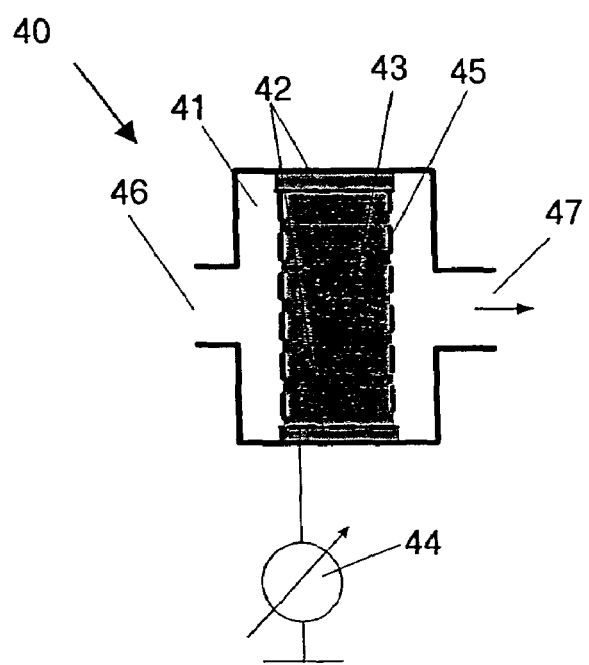
FIG. 4 a measurement arrangement for measuring the total current, i.e. the total charge per unit of time, FIG. 5 a total schematic view, FIG. 6 a measurement arrangement for measuring the total carbon quantity, FIG. 7 a preferred variation of the embodiment of the measurement arrangement according to FIG. 6.

The implementation of the measurement of the total charging is effected in a manner known per se according to the principle of the aerosol electrometer. Here, the particles are collected in a filter which is mounted in an electrically insulated manner, and the current arising thereby is measured, as has already been done with the sensors mentioned further above. FIG. 4 shows one example of an aerosol electrometer 40. In a tight, electrically conductive housing 41 with an aerosol inlet 46 and an outlet 47, the aerosol particles are captured in a filter 43. The filter is either electrically conductive itself or is installed in a conductive housing 45 (Faraday cage) which is permeable to the flow. It is mounted in an insulated manner (insulator 42) and is connected to an ammeter 44. The measured current corresponds to the total charging per unit of time.

Figure 5:
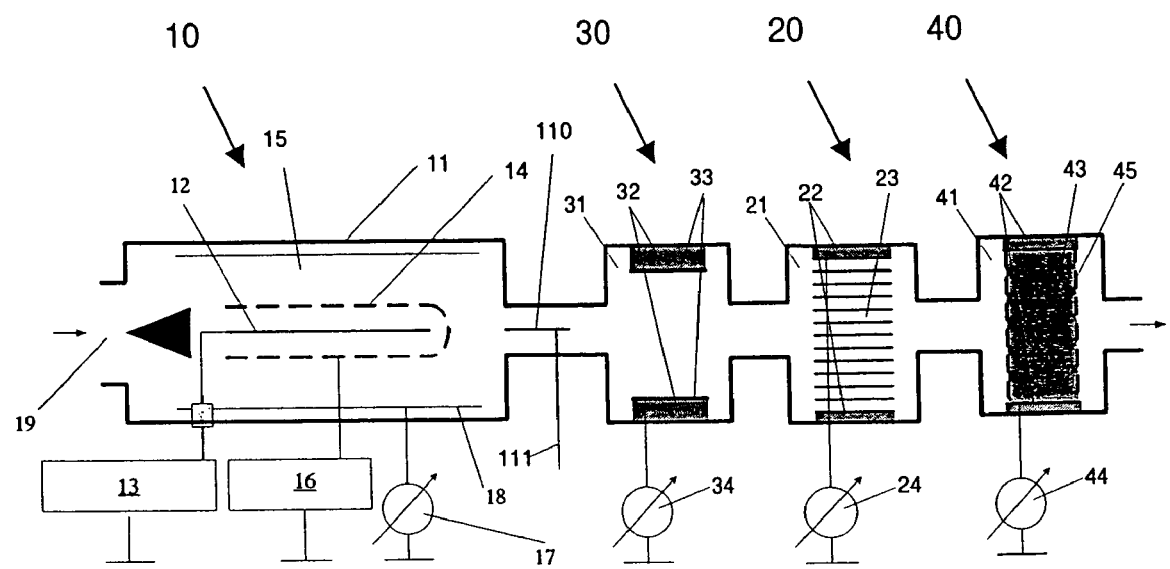

One possible combination of part systems in FIGS. 1-4 is shown in FIG. 5, wherein the reference numerals used in the FIGS. 1 to 4 indicate corresponding elements in FIG. 5. The means for measuring the influence current 30, the diffusional precipitator 20 and the aerosol electrometer 20 are arranged sequentially in the flow direction following the diffusion charger 10. Other arrangements are likewise conceivable, as already mentioned.

Many further ways in realising the invention are conceivable apart from the embodiment described here. For example, the diffusion charger may be present in an embodiment different to that described; the state of the art for example includes many possibilities of realizing a diffusion charger. The electrode for the influence correction does not essentially need to have the same shape as the diffusional precipitator, but may have any shape which does not entail any significant precipitation. For example, it may have the shape of a coarse grid which is mounted in front of the diffusion charger and which in the extreme case consists of only two rods.

Figure 6:
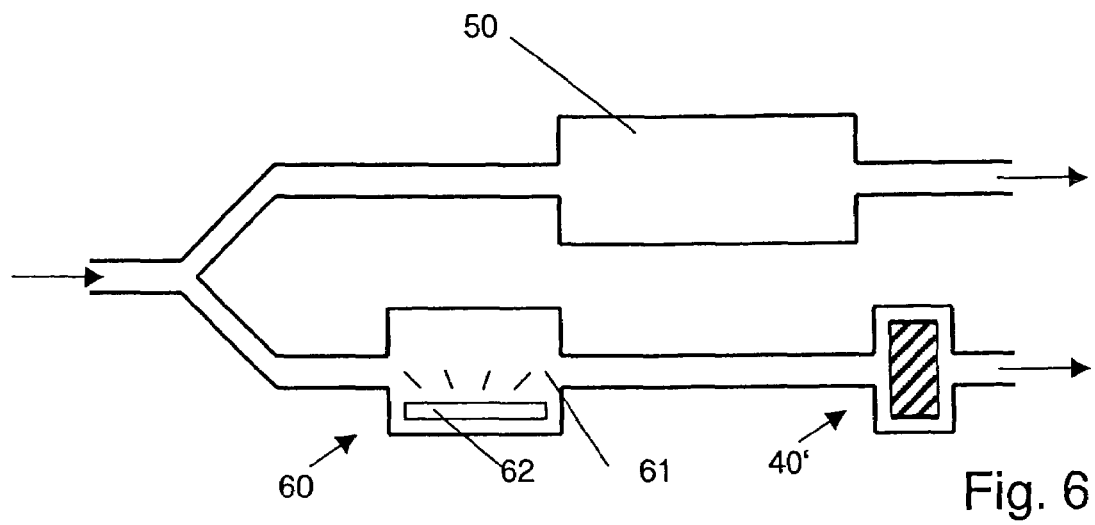

A measurement arrangement, which permits the evaluation of the elementary carbon total quantity, is drawn in FIG. 6. According to the arrangement, each one of two measurement lines is fed with a part flow of the aerosol to be characterised. In the first measurement line, the aerosol is characterised by a device for the measurement of an average particle size 50. The average particle size is represented as the average particle diameter. In a second measurement line, particles are electrically charged by way of a photoelectric charger 60 and subsequently their total charging per unit of time is measured in an aerosol electrometer 40'. The photoelectric charger has a UV light source 62 arranged in a charging chamber 61. The average particle size determined in the device 50 and the total charging measured by the aerosol electrometer 40' are used by an evaluation unit (not drawn), in order to determine a value for the elementary carbon total quantity.

Figure 7:
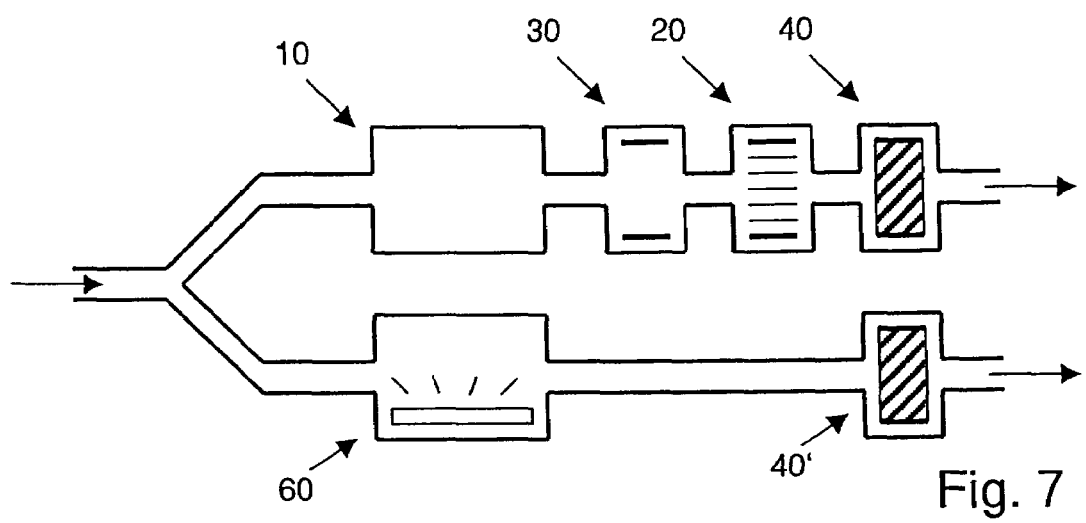

Yet another embodiment of the measurement arrangement according to FIG. 6 is represented in FIG. 7, in which the device for measuring the average particle size 50 according to FIG. 5 is designed. This combination is particularly preferred.

What is claimed is:

1. A method for measuring an integral total number concentration of particles in an aerosol, wherein the aerosol contains particles of an unknown size distribution, the method comprising the steps of:
   electrically charging the aerosol by way of diffusion charging to create charged aerosol particles;
   measuring a diffusional precipitator current which is caused by at least some of the charged aerosol particles being precipitated in a single diffusional precipitator or in a plurality of diffusional precipitators connected electrically in parallel or in a plurality of diffusional precipitators arranged in parallel with regards to an aerosol flow, and
   evaluating a value for the integral total number concentration based on a result from said measurement,
   wherein the said diffusional precipitator current is measured from a single diffusional precipitator and is the only diffusional precipitator current used in said step of evaluating the value of the integral total number concentration.

2. The method according to claim 1, wherein the charging of the aerosol is effected by way of a unipolar diffusion charger.

3. The method according to claim 1, wherein a single diffusional precipitator is used.

4. The method according to claim 1, wherein the diffusional precipitator is designed as a plate precipitator, as a grid precipitator, as a tube precipitator or as a combination of at least one of a plate precipitator, a grid precipitator and of a tube precipitator.

5. The method according to claim 1, comprising the additional step of compensating an influence current which possibly arises in the diffusional precipitator, the step of compensating the influence current including measuring an influence current in an additional electrode, wherein for the calculation of the value for the number concentration, the current measured in the additional electrode is used as a further input value in addition to the result of said measurement of the diffusional precipitator current, said additional step being performed upstream or downstream or in parallel to the step of measuring said diffusional precipitator current.

6. The method according to claim 5, wherein a geometric shape of the additional electrode corresponds to a geometric shape of the diffusional precipitator without precipitation surfaces.

7. The method according to claim 5 wherein the diffusional precipitator and the additional electrode are provided in a serial arrangement and are flowed through consecutively.

8. The method according to claim 1 comprising the additional step of measuring a total current of the diffusion charged aerosol, and of determining the average diameter of the particles from this total current and the diffusional precipitator current.

9. The method according to claim 1 comprising the additional step of compensating an influence current which possibly arises in the diffusional precipitator, the step of compensating the influence current comprising measuring an influence current in an additional electrode, wherein for the calculation of the value for the number concentration, the current measured in the additional electrode is used as a further input value in addition to the result of said measurement of the diffusional precipitator current, said step of compensating the influence current being performed upstream or downstream or in parallel to the step of measuring said diffusional precipitator current, and further comprising the additional step of measuring a total current of the diffusion charged aerosol, and of determining the average diameter of the particles from this total current and the diffusional precipitator current.

10. The method according to claim 9, comprising the additional steps of charging, in a separate measurement line, particles of the aerosol photoelectrically, of determining the charging and of computing an elementary carbon total quantity from this and the average particle diameter.

11. The method according to claim 1 comprising the additional step of measuring a total current of the diffusion charged aerosol, and of determining the average diameter of the particles from this total current and the diffusional precipitator current, and further comprising the additional steps of charging, in a separate measurement line, particles of the aerosol photoelectrically, of determining the charging and of computing an elementary carbon total quantity from this and the average particle diameter.

12. The method according to claim 1, wherein the value for the number concentration is determined, in that the current in the diffusional precipitator is multiplied by a calibration factor and where appropriate is corrected by way of correction values gained from measurements of at least one of the influence current and of the total current.

* * * * *